(12) United States Patent
Davidson et al.

(10) Patent No.: US 11,801,278 B2
(45) Date of Patent: Oct. 31, 2023

(54) METHOD FOR OBTAINING AN EXTRACT OF A PLANT BIOMASS

(71) Applicant: CURE Pharmaceutical, Inc., Oxnard, CA (US)

(72) Inventors: Robert Davidson, Oxnard, CA (US); Vered Gigi, Oxnard, CA (US); Jose Bernardo, Oxnard, CA (US)

(*) Notice: Subject to any disclaimer, the term of this patent is extended or adjusted under 35 U.S.C. 154(b) by 271 days.

(21) Appl. No.: 17/193,261

(22) Filed: Mar. 5, 2021

(65) Prior Publication Data

US 2021/0275618 A1 Sep. 9, 2021

Related U.S. Application Data

(60) Provisional application No. 62/985,474, filed on Mar. 5, 2020.

(51) Int. Cl.
| | |
|---|---|
| *A61K 36/185* | (2006.01) |
| *A61K 36/00* | (2006.01) |
| *A61K 36/07* | (2006.01) |
| *A61K 31/675* | (2006.01) |
| *A61K 31/4045* | (2006.01) |

(52) U.S. Cl.
CPC ........ *A61K 36/185* (2013.01); *A61K 31/4045* (2013.01); *A61K 31/675* (2013.01); *A61K 36/07* (2013.01); *A61K 2236/15* (2013.01); *A61K 2236/31* (2013.01); *A61K 2236/37* (2013.01); *A61K 2236/51* (2013.01); *A61K 2236/53* (2013.01); *A61K 2236/55* (2013.01)

(58) Field of Classification Search
None
See application file for complete search history.

(56) References Cited

U.S. PATENT DOCUMENTS

| | | | |
|---|---|---|---|
| 10,729,706 B2 * | 8/2020 | Küçüksen | A61K 31/4045 |
| 2019/0254988 A1 * | 8/2019 | Archibald | A61K 47/10 |

OTHER PUBLICATIONS

Hilah Bahcetepe (HempIndustryDaily of "Hemp extraction to mushroom extraction? Why some say the pivot is natural", website: Hemp extraction to mushroom extraction? Why some say the pivot is natural (hempindustrydaily.com), published Feb. 4, 2022, pp. 1-3) (Year: 2022).*

* cited by examiner

*Primary Examiner* — Terry A McKelvey
*Assistant Examiner* — Randall O Winston
(74) *Attorney, Agent, or Firm* — Carlson, Caspers, Vandenburgh & Lindquist, P.A.

(57) ABSTRACT

Provided herein is a method of obtaining an extract from a plant biomass as well as an extract obtained from the method. Also provided is a pharmaceutical product, ODF, nutraceutical product, and/or edible product, that includes the extract and one or more excipients. Also provided is a method that includes orally administering the extract (or pharmaceutical product, ODF, nutraceutical product, and/or edible product, that includes the extract).

25 Claims, No Drawings

METHOD FOR OBTAINING AN EXTRACT OF A PLANT BIOMASS

RELATED U.S. APPLICATION DATA

This application claims priority from U.S. Provisional Patent Application 62/985,474 filed on Mar. 5, 2020, the contents of which are incorporated by reference herein it its entirety.

SUMMARY OF THE INVENTION

The present invention provides for a method of obtaining an extract, the method includes: (a) reducing the size of a plant biomass, the plant biomass including psilocybin mushroom; (b) ultrasonicating the plant biomass; (c) contacting the plant biomass with a supercritical fluid solvent system above the critical pressure and above the critical temperature; and (d) removing the supercritical fluid solvent system from the plant biomass to obtain an extract of psilocybin mushroom.

The present invention also provides for a method of obtaining an extract, the method includes: (a) reducing the size of a plant biomass, the plant biomass including psilocybin mushroom and *cannabis*; (b) ultrasonicating the plant biomass; (c) contacting the plant biomass with a supercritical fluid solvent system above the critical pressure and above the critical temperature; and (d) removing the supercritical fluid solvent system from the plant biomass to obtain an extract of psilocybin mushroom and *cannabis*.

The present invention also provides for a method of obtaining an extract, the method includes: (a) reducing the size of a plant biomass, the plant biomass including psilocybin mushroom and *cannabis*; (b) ultrasonicating the plant biomass; (c) contacting the plant biomass with a supercritical fluid solvent system above the critical pressure and above the critical temperature; and (d) removing the supercritical fluid solvent system from the plant biomass to obtain an extract of psilocybin mushroom and *cannabis*; wherein, the plant biomass includes the psilocybin mushroom and the *cannabis* in a weight ratio of 1:99 to 25:75, respectively.

The present invention also provides for a method for obtaining an extract, the method includes: (a) reducing the size of a plant biomass, the plant biomass including psilocybin mushroom and *cannabis*; (b) ultrasonicating the plant biomass; (c) contacting for period of time of at least 60 seconds the plant biomass with a supercritical fluid solvent system that includes carbon dioxide ($CO_2$), at a pressure of at least 74 bar, and at a temperature of at least 31° C.; and (d) removing the supercritical fluid solvent system from the plant biomass to obtain an extract of psilocybin mushroom and *cannabis*; wherein, relative to the plant biomass, the extract is enriched with cannabinoids; relative to the plant biomass, the extract is enriched with at least one of psilocybin, psilocin, and baeocystin; relative to the plant biomass, the extract is enriched with terpenes; and relative to the plant biomass, the extract is enriched with flavonoids.

The present invention also provides for an extract obtained from the method described herein.

The present invention also provides for a pharmaceutical product that includes (i) one or more pharmaceutically acceptable excipients, and (ii) an extract obtained from the method described herein.

The present invention also provides for an oral dissolvable film (ODF) that includes (i) one or more pharmaceutically acceptable excipients, and (ii) an extract obtained from the method described herein.

The present invention also provides for an oral dissolvable film (ODF) that includes (i) a film-forming matrix that includes one or more polymers, and (ii) an extract obtained from the method described herein.

The present invention also provides for an oral dissolvable film described herein, that includes a low dose or microdose of the psychedelic compound.

The present invention also provides for a nutraceutical product that includes (i) one or more nutraceutically acceptable excipients, and (ii) an extract obtained from the method described herein.

The present invention also provides for an edible product that includes (i) one or more edible (e.g., GRAS) excipients, and (ii) an extract obtained from the method described herein.

The present invention also provides for a method of treating in a subject a disease or disorder ameliorated by a psychedelic compound and/or by a cannabinoid. The method includes orally administering to the subject the extract obtained from the method described herein, in an amount and for a period of time sufficient to effectively treat the disease or disorder.

The present invention also provides for a method of treating in a subject a psychological or neurological disorder. The method includes orally administering to the subject the extract obtained from the method described herein, in an amount and for a period of time sufficient to effectively treat the psychological or neurological disorder.

The present invention also provides for a method that includes orally administering to a subject an oral dissolvable film described herein, wherein the oral dissolvable film includes a low dose or microdose of the psychedelic compound and optionally a cannabinoid.

DETAILED DESCRIPTION OF THE INVENTION

Provided herein is a method of obtaining an extract from a plant biomass, as well as an extract obtained from the method. Also provided is a pharmaceutical product, ODF, nutraceutical product, and/or edible product, that includes the extract and one or more excipients. Also provided is a method that includes orally administering the extract (or pharmaceutical product, ODF, nutraceutical product, and/or edible product, that includes the extract).

Across multiple embodiments, the method of obtaining an extract as described herein (and the extract obtained therein, as well as the pharmaceutical product, oral dissolvable film, nutraceutical product, and/or edible product that includes the extract, and the method of medical treatment that includes administering the extract, pharmaceutical product, oral dissolvable film, nutraceutical product, and/or edible product), can independently possess one or more advantages. For example, in specific embodiments, the method of obtaining an extract as described herein can be carried out under conditions (e.g., low temperature, anhydrous solvent system, etc.) to decrease the occurrence of degradation of the desired compound(s) from the plant biomass. In specific embodiments, the method of obtaining an extract as described herein can be carried out without the use of a volatile organic compound (VOC). In specific embodiments, the method of obtaining an extract as described herein can be carried out with a plant biomass containing a desired amount (e.g., weight ratio) of psilocybin mushroom and *cannabis*. This will allow for an extract obtained therein having the desired compound(s) in preferred amount(s). By selecting the plant biomass with a specified ratio of psilocybin mushroom and

*cannabis*, one can target the extract obtained therein as having the desired compound(s) in preferred amount(s). In specific embodiments, the method of obtaining an extract as described herein can provide for an extract that is relatively pure. For example, in specific embodiments, the method of obtaining an extract as described herein can provide for an extract that is essentially free from pesticides, heavy metals, microbials, volatile organic compounds (VOCs), and/or chlorophylls. In specific embodiments, the method of obtaining an extract as described herein can be carried out in a batch production mode, on a relatively large scale (e.g., at least about 1 kg of plant biomass). In specific embodiments, the extract obtained therein can be directly employed in the manufacture of a pharmaceutical product, oral dissolvable film, nutraceutical product, and/or edible product. In doing so, the extract can include a micro-dose, low dose, or large dose of the psychedelic compound(s). In specific embodiments, the method of obtaining an extract as described herein can be carried out in multiple batches. In doing so, the multiple extracts obtained therein can include different amounts of the desired compound(s). Additionally, each of the multiple extracts obtained therein can be included in separate pharmaceutical products, oral dissolvable films, nutraceutical products, and/or edible products, each having different amounts of the desired compound(s). This would allow for the manufacture of products containing different strengths of the desired compound(s). This would also allow for a dosing regimen that includes administering to a subject the multiple products (e.g., each containing a micro-dose, low dose, or large dose of the psychedelic compound(s)). Additionally, in specific embodiments, the method of obtaining an extract is carried out in a batch mode, wherein the one or more batches are carried out in a relatively short period of time (e.g., within 2.5 hours).

As used herein, the following terms have the meanings ascribed to them unless specified otherwise.

The words "comprise," "comprising," "include," "including," and "includes" when used in this specification and claims are intended to specify the presence of stated substances, features, integers, components, or steps, but they do not preclude the presence or addition of one or more other substances, features, integers, components, steps, or combinations thereof.

The term "about" modifies the subject values, such that they are within an acceptable error range, as determined by one of ordinary skill in the art, which will depend in part on the limitations of the measurement system.

The term "treating" (and equivalent terms such as "treat," "treated," and "treatment") of a subject includes the administration of an active pharmaceutical ingredient (API), or a unit dosage form containing the same (e.g., oral dissolvable film), to a subject with the purpose of preventing, curing, healing, alleviating, relieving, altering, remedying, ameliorating, improving, stabilizing or affecting a disease or disorder, or a symptom of a disease or disorder.

The term "subject" refers to living organisms such as humans, dogs, cats, and other mammals. Administration of the medicaments included in the oral dissolvable films of the present invention can be carried out at dosages and for periods of time effective for the treatment of the subject. In some embodiments, the subject is a human. Unless otherwise specified, the human subject can be a male or female, and can further be an adult, adolescent, child, toddler, or infant.

The term "oral administration" or "PO" refers to a route of administration where a substance is taken through the mouth. Many medications are taken orally because they are intended to have a systemic effect, reaching different parts of the body via the bloodstream.

The term "pharmaceutically acceptable" refers to those compounds, excipients, active ingredients, materials, compositions, and/or dosage forms that are, within the scope of sound medical judgment, suitable for use in contact with the tissues of human beings and animals without excessive toxicity, irritation, allergic response, or other problems or complications commensurate with a reasonable benefit/risk ratio.

The term "disintegration" refers to a substance (e.g., matrix of an oral dissolvable film) breaking up or falling apart. The substance will lose cohesion or strength and can fragment into pieces. When placed in the mouth, the substance will break apart in the saliva.

The term "oral dissolvable film" (alternatively known as oral dissolvable films, ODFs, orally dissolving film strips, edible films, edible strips, oral film strips, oral drug strips, buccal films, sublingual films, oral soluble films, etc.) refers to a unit dosage form in which the dissolvable film is specifically configured for oral administration. Oral dissolvable films are composed of pharmaceutically acceptable ingredients that are edible or ingestible. The oral dissolvable film can be configured for multi- or unidirectional release. Similar in size and shape to a postage stamp, oral dissolvable films are designed for oral administration, with the user placing the strip on the tongue (enteric), under the tongue (sublingual), through the oral mucosa (mucosal), against the inside of the cheek (buccal), or on the gums (gingival). Aside from the enteric route, these drug delivery options allow the medication to bypass the first pass metabolism thereby making the medication more bioavailable. As the film dissolves, the drug can enter the blood stream enterically, mucosally, buccally, gingivally, and/or sublingually. As such, the oral dissolvable film is prepared using hydrophilic polymers that dissolves on the tongue or buccal cavity, delivering the drug to the systemic circulation via dissolution when contact with liquid is made. Oral film drug delivery accordingly uses a dissolving film to administer drugs via absorption in the mouth (buccally, sublingually, or gingivally) and/or via the small intestines (enterically). Especially for drugs which are metabolized extensively by the first-pass effect, oral films described herein provide an opportunity for a faster-acting and better absorption profile. The increased bioavailability may also allow for a reduction in adverse events.

The term "psilocybin mushroom," also known as "magic mushroom" or "psychedelic mushroom," refers to one of a polyphyletic group of fungi that contain psilocybin and psilocin. Biological genera containing psilocybin mushrooms include *Copelandia, Gymnopilus, Inocybe, Panaeolus, Pholiotina, Pluteus*, and *Psilocybe*. The effects of psilocybin mushrooms come from psilocybin and psilocin. When psilocybin is ingested, it is broken down to produce psilocin, which is responsible for the psychedelic effects.

Dosage of mushrooms containing psilocybin depends on the potency of the mushroom (the total psilocybin and psilocin content of the mushrooms), which varies significantly both between species and within the same species, but is typically around 0.5-2.0 wt. % of the dried weight of the mushroom.

The concentration of active psilocybin mushroom compounds varies not only from species to species, but also from mushroom to mushroom inside a given species, subspecies or variety. The same holds true even for different parts of the same mushroom. In the species *Psilocybe samuiensis*, the dried cap of the mushroom contains the most psilocybin at about 0.23 wt. %-0.90 wt. %. The mycelium contains about 0.24 wt. %-0.32 wt. %.

The term "psilocybin" refers to a naturally occurring psychedelic prodrug compound produced by more than 200 species of mushrooms, collectively known as psilocybin mushrooms. The most potent are members of the genus *Psilocybe*, such as *P. azurescens, P. semilanceata,* and *P. cyanescens*, but psilocybin has also been isolated from about a dozen other genera. As a prodrug, psilocybin is quickly converted by the body to psilocin, which has mind-altering effects similar, in some aspects, to those of LSD, mescaline, and DMT. In general, the effects include euphoria, visual and mental hallucinations, changes in perception, a distorted sense of time, and spiritual experiences, and can also include possible adverse reactions such as nausea and panic attacks.

The term "psilocin" (also known as 4-HO-DMT, 4-hydroxy DMT, psilocine, psilocyn, or psilotsin) refers to a substituted tryptamine alkaloid and a serotonergic psychedelic substance. It is present in most psychedelic mushrooms together with its phosphorylated counterpart psilocybin.

The term "baeocystin" refers to a psilocybin mushroom alkaloid and analog of psilocybin. It is found as a minor compound in most psilocybin mushrooms together with psilocybin, norbaeocystin, and psilocin. Baeocystin is an N-demethylated derivative of psilocybin, and a phosphorylated derivative of 4-HO-NMT (4-hydroxy-N-methyltryptamine).

The term "*Cannabis*" refers to a genus of flowering plants in the family Cannabaceae. The number of species within the genus is disputed. Three species may be recognized: *Cannabis sativa, Cannabis indica,* and *Cannabis ruderalis; C. ruderalis* may be included within *C. sativa*; all three may be treated as subspecies of a single species, *C. sativa*; or *C. sativa* may be accepted as a single undivided species. The plant is also known as hemp, although this term is often used to refer only to varieties of *Cannabis* cultivated for non-drug use. *Cannabis* has long been used for hemp fiber, hemp seeds and their oils, hemp leaves for use as vegetables and as juice, medicinal purposes, and as a recreational drug. Industrial hemp products are made from *Cannabis* plants selected to produce an abundance of fiber.

The term "biomass" refers to a plant material or plant matter, in whole or in part, useful as a starting material (raw material) in a manufacturing process. The biomass can include psilocybin mushroom. Alternatively, the biomass can include psilocybin mushroom and *cannabis*. As such, "*cannabis* biomass" refers to a *cannabis* plant material, in whole or in part, useful as a starting material (raw material) in a manufacturing process. Likewise, "psilocybin mushroom biomass" or "psilocybin biomass" refers to a psilocybin mushroom material, in whole or in part, useful as a starting material (raw material) in a manufacturing process.

As used herein, "size" refers to the magnitude or dimensions of an item. More specifically, geometrical size (or spatial size) can refer to linear dimensions (length, width, height, diameter, perimeter), area, or volume of an item. Within the context of the present invention, the size refers to the linear dimensions of the plant biomass. In specific embodiments, the plant biomass can be reduced to a desired size (diameter). This size reduction can be carried out, e.g., by blending, grinding, pulverizing, mincing, liquefying, cutting, macerating, and/or chopping the plant biomass. The resulting plant biomass will have a desired size, as measured by the average particle size. There are several methods for measuring particle size and particle size distribution. Within the context of the present invention, "average particle size" refers to a weight average and the linear dimension(s) can be measured with the use of sieves.

The term "reducing the size" refers to decreasing the length, width, and/or thickness of plant matter. In specific embodiments, the reducing of the size can be carried out such that the plant matter has a smaller length, width, and thickness. In further specific embodiments, the reducing of the size can be carried out such that a specified amount (e.g., at least 10 wt. %) of the plant matter has a smaller length, width, and thickness. In specific embodiments, the reducing of the size can be carried out employing at least one of blending, grinding, pulverizing, mincing, liquefying, cutting, macerating, and chopping.

The term "ultrasonicating" or "sonicating" refers to the act of applying sound energy to agitate particles in plant matter, for various purposes such as the extraction of compound(s) from the plant matter. Ultrasonic frequencies (>20 kHz) are often used, leading to the process also being known as ultrasonication or ultra-sonication. It is usually applied using an ultrasonic bath or an ultrasonic probe, colloquially known as a sonicator.

The term "ultrasound" refers to sound waves with frequencies higher than the upper audible limit of human hearing. Ultrasound is not different from "normal" (audible) sound in its physical properties, except that humans cannot hear it. This limit varies from person to person and is approximately 20 kilohertz (20,000 hertz) in healthy young adults. Ultrasound devices operate with frequencies from 20 kHz up to several gigahertz. Ultrasound is defined by the American National Standards Institute as "sound at frequencies greater than 20 kHz". In air at atmospheric pressure, ultrasonic waves have wavelengths of 1.9 cm or less.

The term "cell lysis" refers to the breaking down of the membrane of a cell, often by viral, enzymic, or osmotic mechanisms that compromise its integrity. A fluid containing the contents of lysed cells is called a lysate. One method that can be employed is "Acoustic Lysis," which refers to a method that uses ultrasonic waves to generate areas of high and low pressure which causes cavitation and in turn, cell lysis.

The term "contacting" refers to the act of coming together or touching, as of objects or surfaces. It is the state or condition of touching or of immediate proximity. Within the context of the method for obtaining an extract as described herein, the contacting of the plant biomass with a supercritical fluid solvent system refers to the act of touching or of bringing into an immediate proximity the plant biomass and the supercritical fluid solvent system. For example, the plant biomass can be added to the supercritical fluid solvent system. Alternatively, the supercritical fluid solvent system can be added to the plant biomass.

The term "removing" refers to the act of taking away, separating, or moving to another place or location. Within the context of the method for obtaining an extract as described herein, the removing of the supercritical fluid solvent system from the plant biomass refers to the act of taking away the supercritical fluid solvent system from the plant biomass (or taking away the plant biomass from the supercritical fluid solvent system), such that they no longer contact one another.

The term "moisture content" refers to the quantity of water that exists in a substance. The moisture content is typically expressed as a weight percentage.

The term "enriched" refers to a substance having an increased amount of a desired material or compound(s). For example, within the context of the present invention, the extract can be enriched with: (i) psychedelic compound(s), (ii) cannabinoid(s), (iii) psilocybin, (iv) psilocin (v) baeocystin, (vi) terpene(s), (vii) flavonoid(s), or (viii) any combination thereof. Specifically, relative to the plant biomass, on a weight percentage basis, the extract can have an increased amount of any one of more of (i)-(viii) above.

In specific embodiments, the method of obtaining an extract as described herein can be carried out in a batch mode (alternatively referred to as "batch production"). As used herein, "batch mode" refers to a method of manufacturing where the products are made as specified groups or amounts, within a time frame. A batch can go through a series of steps in a large manufacturing process to make the final desired product. Batch production is used for many types of manufacturing that may need smaller amounts of production at a time to ensure specific quality standards or changes in the process. This is opposed to large mass production or continuous production methods where the product or process does not need to be checked or changed as frequently or periodically. Within the context of the present invention, a batch production can be carried out on a scale of up to about 1 kg of plant biomass. Additionally, a batch production can be carried out within a relatively short period of time (e.g., within 1.5 hours).

The term "weight ratio" refers to the relative weight of two substances. Specifically, within the context of the plant biomass employed in the method for obtaining an extract, the psilocybin mushroom and the *cannabis* can be present in a specified weight ratio. For example, the psilocybin mushroom and the *cannabis* can be present in a weight ratio of at least 1:99. Meaning, for every gram of plant biomass, the psilocybin mushroom will be present in at least 0.01 grams (or at least 10 mg).

The term "pharmaceutical product" refers to any substance that causes a change in an organism's physiology or psychology when consumed. The pharmaceutical product can be used to treat, cure, or prevent a disease or to promote well-being. The pharmaceutical product can also be taken to cure or ameliorate any symptoms of an illness or medical condition. The pharmaceutical product will include the extract as described herein (or is manufactured from the extract), in combination with one or more pharmaceutically acceptable excipients.

The term "nutraceutical product" refers to a product which claims physiological benefits when consumed. The nutraceutical product will include the extract as described herein (or is manufactured from the extract), in combination with one or more nutraceutically acceptable excipients.

The term "edible product" refers to an ingestible or food product containing the extract as described herein (or is manufactured from the extract).

The term "psychedelic compound" refers to any of the naturally occurring compounds present in the psilocybin mushroom plant, having psychedelic activity when administered to a subject. Specific psychedelic compounds present in psilocybin mushrooms include psilocybin, psilocin, and baeocystin.

The term "low dose" refers to the quantity of active ingredient that is within the therapeutic window but is below the optimal biological dose. Meaning, it is the range of active ingredient dosages which can treat disease effectively without having toxic effects but is below the dose that will most effectively produce the desired effect while remaining in the range of acceptable toxicity. For example, in specific embodiments, a small dose of psychedelic compound (e.g., psilocin, psilocybin, and/or baeocystin), in the aggregate, is 10±2 mg.

The term "microdose" refers to the quantity of active ingredient that is below the therapeutic window and is below the optimal biological dose. Meaning, it is the below the range of active ingredient dosages which can treat disease effectively without having toxic effects and is also below the dose that will most effectively produce the desired effect while remaining in the range of acceptable toxicity. For example, in specific embodiments, a microdose of psychedelic compound (e.g., psilocin, psilocybin, and/or baeocystin), in the aggregate, is 10-30 mcg.

The term "sub-therapeutic" refers to the quantity of active ingredient considered by the prescribing medical practitioner to be below the therapeutic window.

The term "large dose" refers to the quantity of active ingredient that is within the therapeutic window and is also within the optimal biological dose. Meaning, it is the range of active ingredient dosages which can treat disease effectively without having toxic effects and is also the dose that will most effectively produce the desired effect while remaining in the range of acceptable toxicity. For example, in specific embodiments, a large dose of psychedelic compound (e.g., psilocin, psilocybin, and/or baeocystin), in the aggregate, is 25±5 mg.

The "term therapeutic index (TI)" is a quantitative measurement of the relative safety of an active ingredient. It is a comparison of the amount of an active ingredient that causes the therapeutic effect to the amount that causes toxicity. The related terms therapeutic window or safety window refer to a range of doses which optimize between efficacy and toxicity, achieving the greatest therapeutic benefit without resulting in unacceptable side-effects or toxicity. TI refers to the ratio of the dose of drug that causes adverse effects at an incidence/severity not compatible with the targeted indication (e.g. toxic dose in 50% of subjects, TD50) to the dose that leads to the desired pharmacological effect (e.g. efficacious dose in 50% of subjects, ED50). In contrast, in a drug development setting TI is calculated based on plasma exposure levels. The therapeutic window (or pharmaceutical window) of a drug is the range of drug dosages which can treat disease effectively without having toxic effects. Optimal biological dose (OBD) is the quantity of a drug that will most effectively produce the desired effect while remaining in the range of acceptable toxicity.

The term "unit dose" refers to products in the form in which they are marketed for use, with a specific mixture of active ingredients and inactive components (excipients), in a particular configuration (such as an ODF, for example), and apportioned into a particular dose or strength of active ingredient(s).

The term "extraction" refers to a separation process that includes the separation of a substance from a matrix. Common examples include a solid-liquid extraction. The distribution of a solute between two phases is an equilibrium condition described by partition theory. This is based on specifically how the analyte moves from the initial solvent into the extracting solvent. Obtaining substances from psilocybin mushroom and/or *cannabis* is an example of an extraction, where the substances are removed from the plant(s) utilizing supercritical fluid extraction with $CO_2$.

The term "supercritical fluid extraction" or "SFE" refers to the process of separating one component (the extractant) from another (the matrix) using supercritical fluids as the extracting solvent. Extraction is usually from a solid matrix, e.g., plant matter (or biomass). Carbon dioxide ($CO_2$) is the most used supercritical fluid, sometimes modified by co-solvents such as ethanol or methanol. Extraction conditions for supercritical carbon dioxide ($CO_2$) are above the critical temperature of 31° C. and critical pressure of 74 bar. Addition of modifiers or co-solvents may slightly alter this. The properties of the supercritical fluid can be altered by varying the pressure and/or temperature, allowing selective extraction. For example, volatile oils can be extracted from a plant with low pressures (100 bar). Lipids can be removed using pure $CO_2$ at higher pressures, and then phospholipids can be removed by adding ethanol to the solvent.

The term "fractional supercritical fluid extraction" or "FSFE" refers to a supercritical fluid extraction carried out multiple (i.e., two or more) times on the same plant biomass, to provide multiple fractions. The multiple supercritical fluid extractions can be carried out (i) with a different solvent system, (ii) at a different pressure, (iii) at a different temperature, or (iv) any combination of (i)-(iii).

The term "extract" refers to a substance obtained by extracting a part of a raw material (e.g., plant matter or biomass), by using a solvent such as carbon dioxide, ethanol or water. Across various embodiments, the term "extract" includes "extract of psilocybin mushroom and *cannabis*" and "extract of psilocybin mushroom."

The term "full-spectrum extract" or "whole plant extract" refers to an extract of plant biomass that maintains the full profile of the plant(s). Full-spectrum extracts are notoriously difficult to produce. While you need to keep as many of the desirable compounds as possible, you also want to rid the extract of unnecessary components.

The term "broad-spectrum extract" refers to an extract of plant biomass that maintains a broad profile of the plant(s), but the profile is more limiting than the full-spectrum extract. Broad-spectrum extracts are difficult to produce. While you need to keep as many of the desirable compounds as possible, you also want to rid the extract of unnecessary components.

The term "isolate" refers to a relatively pure extract of the plant biomass. The purity can be at least 90 wt. % pure, at least 95 wt. % pure, at least 98 wt. % pure, or at least 99 wt. % pure.

The term "cannabinoid" refers to a class of diverse chemical compounds that act on cannabinoid receptors on cells that repress neurotransmitter release in the brain. These receptor proteins include the endocannabinoids (produced naturally in the body by humans and animals), the phytocannabinoids (found in *Cannabis* and some other plants), and synthetic cannabinoids (manufactured chemically). The most notable cannabinoid is the phytocannabinoid Δ9-tetrahydrocannabinol (THC), the primary psychoactive compound of *Cannabis*. Cannabidiol (CBD) is another major constituent of the plant, representing up to 40% in extracts of the plant resin. There are at least 85 different cannabinoids isolated from *Cannabis*, exhibiting varied effects.

| | Cannabinoids isolated from Cannabis |
|---|---|
| 1. | Cannabigerol ((E)-CBG-C5) |
| 2 | Cannabigerol monomethyl ether ((E)-CBGM-CS A) |
| 3. | Cannabinerolic acid A ((Z)-CBGA-C5 A) |
| 4. | Cannabigerovarin ((E)-CBGV-C3) |
| 5. | Cannabigerolic acid A ((E)-CBGA-C5 A) |
| 6. | Cannabigerolic acid A monomethyl ether ((E)-CBGAM-C5 A) |
| 7. | Cannabigerovarinic acid A ((E)-CBGVA-C3 A) |
| 8. | (+)-Cannabichromene (CBC-C5) |
| 9. | (+)-Cannabichromenic acid ACBCA-C5 A |
| 10. | (+)-Cannabivarichromene or (+)-Cannabichromevarin (CBCV-C3) |
| 11. | (+)-Cannabichromevarinic acid A (CBCVA-C3 A) |
| 12. | (−)-Cannabidiol (CBD-C5) |
| 13. | Cannabidiol momomethyl ether (CBDM-C5) |

| | Cannabinoids isolated from Cannabis |
|---|---|
| 14. | Cannabidiol-C4 (CBD-C4) |
| 15. | (−)-Cannabidivarin CBDV-C3 |
| 16. | Cannabidiorcol (CBD-C1) |
| 17. | Cannabidiolic acid (CBDA-C5) |
| 18. | Cannabidivarinic acid (CBDVA-C3) |
| 19. | Cannabinodiol (CBND-C5) |
| 20. | Cannabinodivarin (CBND-C3) |
| 21. | Δ9-Tetrahydrocannabinol (Δ9-THC-C5) |
| 22. | Δ9-Tetrahydrocannabinol-C4 (Δ9-THC-C4) |
| 23. | Δ9-Tetrahydrocannabivarin (Δ9-THCV-C3) |
| 24. | Δ9-Tetrahydrocannabiorcol (Δ9-THCO-C1) |
| 25. | Δ9-Tetrahydro-cannabinolic acid A (Δ9-THCA-C5 A) |
| 26. | Δ9-Tetrahydro-cannabinolic acid B (Δ9-THCA-CS B) |
| 27. | Δ9-Tetrahydro-cannabinolic acid-C4A and/or B (Δ9-THCA-C4A and/or B) |
| 28. | Δ9-Tetrahydro-cannabivarinic acid A (Δ9-THCVA-C3A) |
| 29. | Δ9-Tetrahydro-cannabiorcolic acid A and/or B (Δ9-THCOA-C1A and/or B) |
| 30. | (−)-Δ8-trans-(6aR, 10aR)-Δ8-Tetrahydrocannabinol (Δ8-THC-C5) |
| 31. | (−)-Δ8-trans-(6aR, 10aR)-Tetrahydrocannabinolic acid A (Δ8-THCA-C5 A) |
| 32. | (−)-(6aS, 10aR)-Δ9-Tetrahydrocannabinol ((−)-cis-Δ9-THC-C5) |
| 33. | Cannabinol (CBN-C5) |
| 34. | Cannabinol-C4 (CBN-C4) |
| 35. | Cannabivarin (CBN-C3) |
| 36. | Cannabinol-C2 (CBN-C2) |
| 37. | Cannabiorcol (CBN-C1) |
| 38. | Cannabinolic acid A (CBNA-C5 A) |
| 39. | Cannabinol methyl ether (CBNM-C5) |
| 40. | (−)-(9R,10R)-trans-Cannabitriol ((−)-trans-CBT-C5) |
| 41. | (+)-(9S, 10S)-Cannabitriol ((+)-trans-CBT-C5) |
| 42. | (±)-(9R,10S/9S,10R)-Cannabitriol ((±)-cis-CBT-C5) |
| 43. | (−)-(9R,10R)-trans-10-O-Ethyl-cannabitriol ((−)-trans-CBT-OEt-C5) |
| 44. | (±)-(9R,10R/9S,10S)-Cannabitriol-C3 ((±)-trans-CBT-C3) |
| 45. | 8,9-Dihydroxy-Δ6a(10a)-tetrahydrocannabinol (8,9-Di-OH-CBT-C5) |
| 46. | Cannabidiolic acid A cannabitriol ester (CBDA-C5 9-OH-CBT-C5 ester) |
| 47. | (−)-(6aR,9S, 10S,10aR)-9,10-Dihydroxy-hexahydrocannabinol, Cannabiripsol (Cannabiripsol-C5) |
| 48. | (−)-6a,7,10a-Trihydroxy-Δ9-tetrahydrocannabinol ((−)-Cannabitetrol) |
| 49. | 10-Oxo-Δ6a(10a)- tetrahydrocannabinol (OTHC) |
| 50. | (5aS,6S,9R,9aR)-Cannabielsoin (CBE-C5) |
| 51. | (5aS,6S,9R,9aR)-C3-Cannabielsoin (CBE-C3) |
| 52. | (5aS,6S,9R,9aR)-Cannabielsoic acid A (CBEA-C5 A) |
| 53. | (5aS,6S,9R,9aR)-Cannabielsoic acid B (CBEA-C5 B) |
| 54. | (5aS,6S,9R,9aR)-C3-Cannabielsoic acid B (CBEA-C3 B) |
| 55. | Cannabiglendol-C3 (OH-iso-HHCV-C3) |
| 56. | Dehydrocannabifuran (DCBF-C5) |
| 57 | Cannabifuran (CBF-C5) |
| 58. | (−)-Δ7-trans-(1R,3R,6R)-Isotetrahydrocannabinol |
| 59. | (±)-Δ7-1,2-cis-(1R,3R,6S/1S,3S,6R)-Isotetrahydro-cannabivarin |
| 60. | (−)-Δ7-trans-(1R,3R,6R)- Isotetrahydrocannabivarin |
| 61. | (±)-(1aS,3aR,8bR,8cR)-Cannabicyclol (CBL-C5) |
| 62. | (±)-(1aS,3aR,8bR,8cR)-Cannabicyclolic acid A (CBLA-C5 A) |
| 63. | (±)-(1aS,3aR,8bR,8cR)-Cannabicyclovarin (CBLV-C3) |
| 64. | Cannabicitran (CBT-C5) |
| 65. | Cannabichromanone (CBCN-C5) |
| 66. | Cannabichromanone-C3 (CBCN-C3) |
| 67. | Cannabicoumaronone (CBCON-CS) |
| 68. | Cannabielsoin acid A (CBEA-A) |
| 69. | 10-Ethoxy-9-hydroxy-delta-6a-tetrahydrocannabinol |
| 70. | Cannabitriolvarin (CBTV) |
| 71. | Delta-9-tetrahydrocannabiorcolic acid (THCA-C1) |
| 72. | Delta-7-cis-iso-tetrahydrocanna |
| 73. | Cannabichromanon (CBCF) |

| Structure of common cannabinoids |
|---|
| 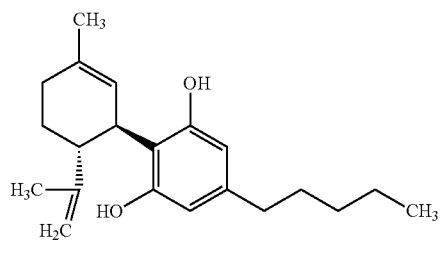 [SMILES: C=C(C)[C@@H]1CCC(C)=C[C@H]1c1c(O)cc(CCCCC)cc1O]<br>CBD |
| 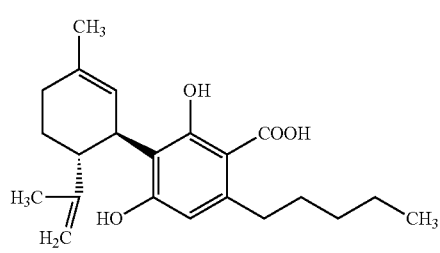 [SMILES: C=C(C)[C@@H]1CCC(C)=C[C@H]1c1c(O)cc(CCCCC)c(C(=O)O)c1O]<br>CBDA |
| 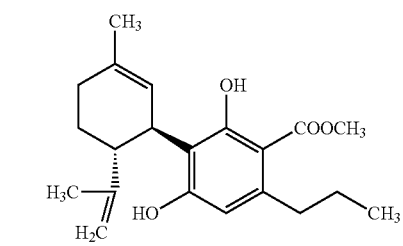 [SMILES: C=C(C)[C@@H]1CCC(C)=C[C@H]1c1c(O)cc(CCC)c(C(=O)OC)c1O]<br>CBDVA-OMe |
| 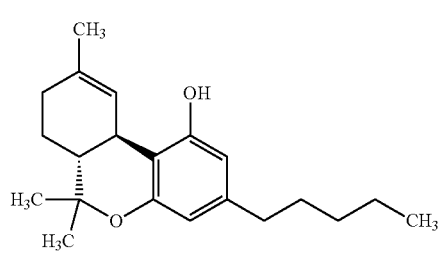<br>THC |
| 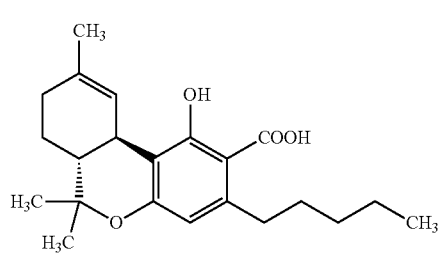<br>THCA |
| Structure of common cannabinoids |
|---|
| 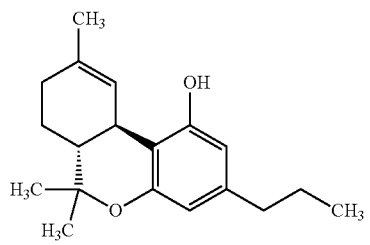<br>THCV |
| 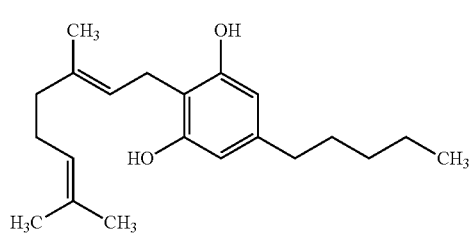 [SMILES: CCCCCc1cc(O)c(C/C=C(\C)CCC=C(C)C)c(O)c1]<br>CBG |
| 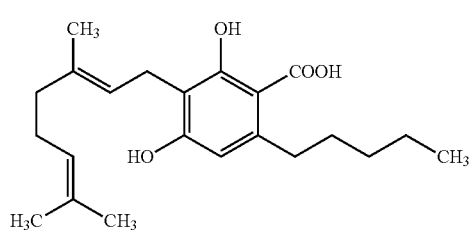 [SMILES: CCCCCc1cc(O)c(C/C=C(\C)CCC=C(C)C)c(O)c1C(=O)O]<br>CBGA |
| 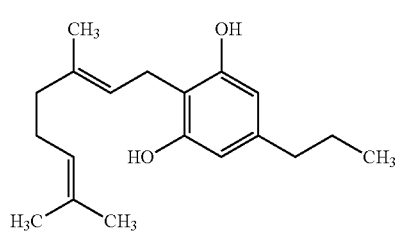 [SMILES: CCCc1cc(O)c(C/C=C(\C)CCC=C(C)C)c(O)c1]<br>CBGV |
| 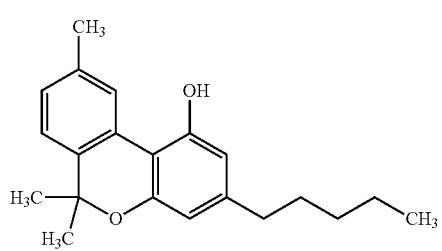 [SMILES: CCCCCc1cc(O)c2c(c1)OC(C)(C)c1ccc(C)cc1-2]<br>CBN |

Structure of common cannaboinoids

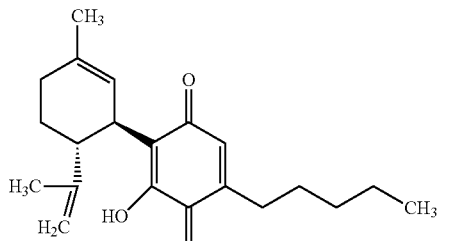
CBQ

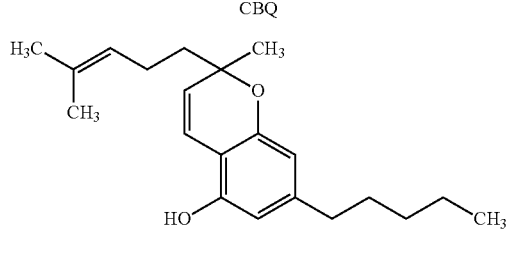
CBC

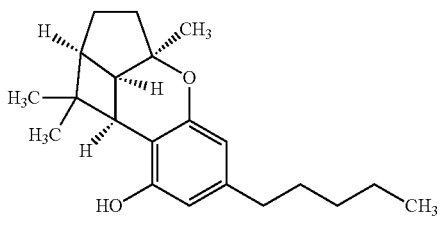
CBL

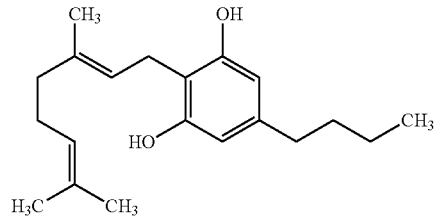 [SMILES: CCCCc1cc(O)c(C/C=C(\C)CCC=C(C)C)c(O)c1]
CBGB

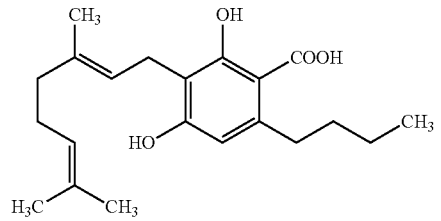 [SMILES: CCCCc1cc(O)c(C/C=C(\C)CCC=C(C)C)c(O)c1C(=O)O]
CBGBA

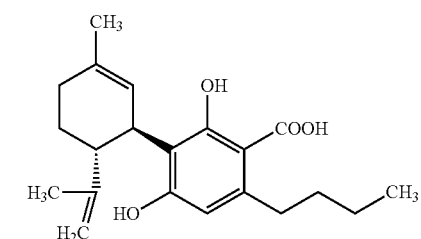
CBDBA

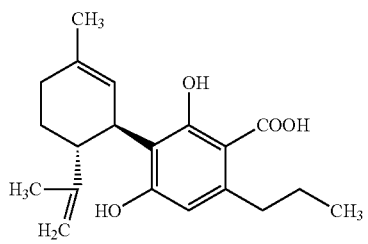 [SMILES: C=C(C)[C@@H]1CCC(C)=C[C@H]1c1c(O)cc(CCC)c(C(=O)O)c1O]
CBDVA

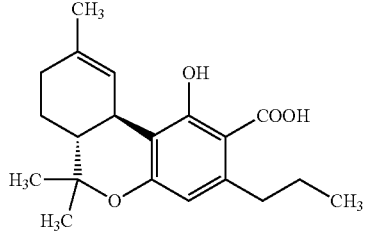
THCVA

The term "terpene" refers to a hydrocarbon or derivative thereof, found as a natural product and biosynthesized by oligomerization of isoprene units. A terpene can be acyclic, monocyclic, bicyclic, or multicyclic. Examples include, e.g., sesquiterpenes (e.g., (−)-β-caryophyllene, humulene, vetivazulene, guaiazulene, longifolene, copaene, and patchoulol), monoterpenes (e.g., limonene and pulegone), monoterpenoids (e.g., carvone), diterpenes (e.g., taxadiene), and triterpenes (e.g., squalene, betulin, betulinic acid, lupane, lupeol, betulin-3-caffeate, allobetulin, and cholesterol). The following are examples of terpenes present in *cannabis* biomass.

| Terpene |
| --- |
| β-myrcene |
| δ-limonene |
| β-caryophyllene |
| β-pinene |
| α-pinene |
| α-terpineol |
| α-humulene |
| camphene |
| fenchone |
| terpinolene |
| α-terpinene |
| 3-carene |
| α-phellandrene |
| borneol |
| fenchol |
| ocimene |
| valencene |

The method for obtaining an extract as described herein can optionally include a subsequent purification of extract. As used herein the term "purifying" (and purification) refers to a process of physical separation of a chemical substance of interest from foreign or contaminating substances. Within the context of the present invention, foreign or contaminating substances desired to be removed can include, e.g., pesticides, heavy metals, microbials, volatile organic compounds (VOCs), and chlorophylls.

Pure results of a successful purification process are termed an "isolate." The following non-exhaustive list of chemical purification methods can be employed within the context of the present invention: filtration, centrifugation, evaporation, liquid-liquid extraction, crystallization, recrystallization, trituration, adsorption, chromatography, and distillation.

As used herein, "filtration" refers to a mechanical method to separate solids from liquids or gases by passing the feed stream through a porous sheet such as a cloth or membrane, which retains the solids and allows the liquid to pass through.

As used herein, "centrifugation" refers to a process that uses an electric motor to spin a vessel of fluid at high speed to make heavier components settle to the bottom of the vessel.

As used herein, "evaporation" refers to a process which removes volatile liquids from non-volatile solutes, which cannot be done through filtration due to the small size of the substances.

As used herein, "liquid-liquid extraction" refers to a process which removes an impurity or recovers a desired product by dissolving the crude material in a solvent in which other components of the feed material are soluble.

As used herein, "crystallization" refers to a process which separates a product from a liquid feed stream, often in extremely pure form, by cooling the feed stream or adding precipitants that lower the solubility of the desired product so that it forms crystals. The pure solid crystals are then separated from the remaining liquor by filtration or centrifugation.

As used herein, "recrystallization" refers to a process in which a desired solid (crystalline) product is dissolved in a very pure solvent, and then crystallized, and the crystals recovered, in order to improve and/or verify their purity.

As used herein, "trituration" refers to as process that removes highly soluble impurities from usually solid insoluble material by rinsing it with an appropriate solvent.

As used herein, "adsorption" refers to a process that removes a soluble impurity from a feed stream by trapping it on the surface of a solid material, such as activated carbon, that forms strong non-covalent chemical bonds with the impurity. Within the context of the present invention, carbon black is a substance suitable for adsorption.

As used herein, "chromatography" refers to a process that employs continuous adsorption and desorption on a packed bed of a solid to purify multiple components of a single feed stream. In a laboratory setting, mixture of dissolved materials are typically fed using a solvent into a column packed with an appropriate adsorbent, and due to different affinities for solvent versus adsorbent the components in the original mixture exit the column in the moving phase at different rates, which thus allows to selectively collect desired materials out of the initial mixture.

As used herein, "distillation" refers to a process that separates one or more volatile liquids on the basis of their relative volatilities. There are several types of distillation: simple distillation, fractional distillation, steam distillation etc.

Specific Embodiments

The specific embodiments describing the subject matter provided below are for illustration purposes only, and do not otherwise limit the scope of the disclosed subject matter, as defined by the claims.

In specific embodiments, the method for obtaining an extract is carried out in a batch production mode.

In specific embodiments, the method for obtaining an extract is carried out in a batch production mode, wherein a batch includes up to 50 kg of the plant biomass.

In specific embodiments, the method for obtaining an extract is carried out in a batch production mode, wherein a batch includes up to 25 kg of the plant biomass.

In specific embodiments, the method for obtaining an extract is carried out in a batch production mode, wherein a batch includes up to 15 kg of the plant biomass.

In specific embodiments, the method for obtaining an extract is carried out in a batch production mode, wherein a batch includes up to 10 kg of the plant biomass.

In specific embodiments, the method for obtaining an extract is carried out in a batch production mode, wherein a batch includes up to 5 kg of the plant biomass.

In specific embodiments, the method for obtaining an extract is carried out in a batch production mode, wherein a batch includes at least 0.5 kg of the plant biomass.

In specific embodiments, the method for obtaining an extract is carried out in a batch production mode, wherein a batch includes at least 1 kg of the plant biomass.

In specific embodiments, the method for obtaining an extract is carried out in a batch production mode, wherein a batch includes at least 5 kg of the plant biomass.

In specific embodiments, the method for obtaining an extract is carried out in a batch production mode, wherein a batch includes at least 10 kg of the plant biomass.

In specific embodiments, the method for obtaining an extract is carried out in a batch production mode, wherein a batch includes at least 15 kg of the plant biomass.

In specific embodiments, the plant biomass includes psilocybin mushroom.

In specific embodiments, the plant biomass includes psilocybin mushroom and *cannabis*.

In specific embodiments, relative to the plant biomass, the extract is enriched with one or more cannabinoids.

In specific embodiments, relative to the *cannabis*, the extract is enriched with one or more cannabinoids.

In specific embodiments, relative to the plant biomass, the extract is enriched with at least one of psilocybin, psilocin, and baeocystin.

In specific embodiments, relative to the psilocybin mushroom, the extract is enriched with at least one of psilocybin, psilocin, and baeocystin.

In specific embodiments, relative to the plant biomass, the extract is enriched with one or more terpenes.

In specific embodiments, relative to the *cannabis*, the extract is enriched with one or more terpenes.

In specific embodiments, relative to the plant biomass, the extract is enriched with one or more flavonoids.

In specific embodiments, relative to the *cannabis*, the extract is enriched with one or more flavonoids.

In specific embodiments, relative to the plant biomass, the extract contains less pesticides, heavy metals, microbials, volatile organic compounds (VOCs), or chlorophylls.

In specific embodiments, relative to the plant biomass, the extract includes at least 10% more in the aggregate of cannabinoids.

In specific embodiments, relative to the *cannabis*, the extract includes at least 10% more in the aggregate of cannabinoids.

In specific embodiments, on a weight basis and relative to the plant biomass, the extract includes at least 10% more in the aggregate of psilocybin, psilocin, and/or baeocystin.

In specific embodiments, on a weight basis and relative to the psilocybin mushroom, the extract includes at least 10% more in the aggregate of psilocybin, psilocin, and/or baeocystin.

In specific embodiments, on a weight basis and relative to the plant biomass, the extract includes at least 10% more in the aggregate of terpenes.

In specific embodiments, on a weight basis and relative to the *cannabis*, the extract includes at least 10% more in the aggregate of terpenes.

In specific embodiments, on a weight basis and relative to the plant biomass, the extract includes at least 10% more in the aggregate of flavonoids.

In specific embodiments, on a weight basis and relative to the *cannabis*, the extract includes at least 10% more in the aggregate of flavonoids.

In specific embodiments, on a weight basis and relative to the plant biomass, the extract contains at least 10% less in the aggregate of pesticides, heavy metals, microbials, volatile organic compounds (VOCs), and/or chlorophylls.

In specific embodiments, on a weight basis and relative to the plant biomass, the extract includes at least 25% more in the aggregate of cannabinoids.

In specific embodiments, on a weight basis and relative to the *cannabis*, the extract includes at least 25% more in the aggregate of cannabinoids.

In specific embodiments, on a weight basis and relative to the plant biomass, the extract includes at least 25% more in the aggregate of psilocybin, psilocin, and/or baeocystin.

In specific embodiments, on a weight basis and relative to the psilocybin mushroom, the extract includes at least 25% more in the aggregate of psilocybin, psilocin, and/or baeocystin.

In specific embodiments, on a weight basis and relative to the plant biomass, the extract includes at least 25% more in the aggregate of terpenes.

In specific embodiments, on a weight basis and relative to the *cannabis*, the extract includes at least 25% more in the aggregate of terpenes.

In specific embodiments, on a weight basis and relative to the plant biomass, the extract includes at least 25% more in the aggregate of flavonoids.

In specific embodiments, on a weight basis and relative to the *cannabis*, the extract includes at least 25% more in the aggregate of flavonoids.

In specific embodiments, on a weight basis and relative to the plant biomass, the extract contains at least 25% less in the aggregate of pesticides, heavy metals, microbials, volatile organic compounds (VOCs), and/or chlorophylls.

In specific embodiments, on a weight basis and relative to the plant biomass, the extract includes at least 50% more in the aggregate of cannabinoids.

In specific embodiments, on a weight basis and relative to the *cannabis*, the extract includes at least 50% more in the aggregate of cannabinoids.

In specific embodiments, on a weight basis and relative to the plant biomass, the extract includes at least 50% more in the aggregate of psilocybin, psilocin, and/or baeocystin.

In specific embodiments, on a weight basis and relative to the psilocybin mushroom, the extract includes at least 50% more in the aggregate of psilocybin, psilocin, and/or baeocystin.

In specific embodiments, on a weight basis and relative to the plant biomass, the extract includes at least 50% more in the aggregate of terpenes.

In specific embodiments, on a weight basis and relative to the *cannabis*, the extract includes at least 50% more in the aggregate of terpenes.

In specific embodiments, on a weight basis and relative to the plant biomass, the extract includes at least 50% more in the aggregate of flavonoids.

In specific embodiments, on a weight basis and relative to the *cannabis*, the extract includes at least 50% more in the aggregate of flavonoids.

In specific embodiments, on a weight basis and relative to the plant biomass, the extract contains at least 50% less in the aggregate of pesticides, heavy metals, microbials, volatile organic compounds (VOCs), and/or chlorophylls.

In specific embodiments, the extract is a full-spectrum extract of psilocybin mushroom and *cannabis*.

In specific embodiments, the extract is a broad-spectrum extract of psilocybin mushroom and *cannabis*.

In specific embodiments, the extract is a full-spectrum extract of psilocybin mushroom.

In specific embodiments, the extract is a broad-spectrum extract of psilocybin mushroom.

In specific embodiments, the extract is an isolate of psilocybin mushroom.

In specific embodiments, the extract includes 1-100 mg THC and 10-30 mcg in the aggregate of psilocin, psilocybin, and baeocystin.

In specific embodiments, the extract includes 1-100 mg THC and 20±10 mcg in the aggregate of psilocin, psilocybin, and baeocystin.

In specific embodiments, the extract includes 1-100 mg THC and 10 mg in the aggregate of psilocin, psilocybin, and baeocystin.

In specific embodiments, the extract includes 1-100 mg THC and 10±2 mg in the aggregate of psilocin, psilocybin, and baeocystin.

In specific embodiments, the extract includes 1-100 mg THC and 25 mg in the aggregate of psilocin, psilocybin, and baeocystin.

In specific embodiments, the extract includes 1-100 mg THC and 25±5 mg in the aggregate of psilocin, psilocybin, and baeocystin.

In specific embodiments, the extract includes 5-75 mg THC and 10-30 mcg in the aggregate of psilocin, psilocybin, and baeocystin.

In specific embodiments, the extract includes 5-75 mg THC and 20±10 mcg in the aggregate of psilocin, psilocybin, and baeocystin.

In specific embodiments, the extract includes 5-75 mg THC and 10 mg in the aggregate of psilocin, psilocybin, and baeocystin.

In specific embodiments, the extract includes 5-75 mg THC and 10±2 mg in the aggregate of psilocin, psilocybin, and baeocystin.

In specific embodiments, the extract includes 5-75 mg THC and 25 mg in the aggregate of psilocin, psilocybin, and baeocystin.

In specific embodiments, the extract includes 5-75 mg THC and 25±5 mg in the aggregate of psilocin, psilocybin, and baeocystin.

In specific embodiments, the extract includes 5-50 mg THC and 10-30 mcg in the aggregate of psilocin, psilocybin, and baeocystin.

In specific embodiments, the extract includes 5-50 mg THC and 20±10 mcg in the aggregate of psilocin, psilocybin, and baeocystin.

In specific embodiments, the extract includes 5-50 mg THC and 10 mg in the aggregate of psilocin, psilocybin, and baeocystin.

In specific embodiments, the extract includes 5-50 mg THC and 10±2 mg in the aggregate of psilocin, psilocybin, and baeocystin.

In specific embodiments, the extract includes 5-50 mg THC and 25 mg in the aggregate of psilocin, psilocybin, and baeocystin.

In specific embodiments, the extract includes 5-50 mg THC and 25±5 mg in the aggregate of psilocin, psilocybin, and baeocystin.

In specific embodiments, a unit dose of the extract includes any one of EMBODIMENTS A-AM as shown below.

| | | Amount of psilocin, psilocybin, and bacocystin (aggregate) | | |
|---|---|---|---|---|
| | | 10-30 mcg (microdose) | 10 ± 2 mg (low dose) | 25 ± 5 mg (high dose) |
| Amount of THC | 1 ± 0.5 mg | EMBODIMENT A | EMBODIMENT B | EMBODIMENT C |
| | 2.5 ± 1.5 mg | EMBODIMENT D | EMBODIMENT E | EMBODIMENT F |
| | 5 ± 2.5 mg | EMBODIMENT G | EMBODIMENT H | EMBODIMENT I |
| | 10 ± 5 mg | EMBODIMENT J | EMBODIMENT K | EMBODIMENT L |
| | 20 ± 5 mg | EMBODIMENT M | EMBODIMENT N | EMBODIMENT O |
| | 30 ± 5 mg | EMBODIMENT P | EMBODIMENT Q | EMBODIMENT R |
| | 40 ± 5 mg | EMBODIMENT S | EMBODIMENT T | EMBODIMENT U |
| | 50 ± 5 mg | EMBODIMENT V | EMBODIMENT W | EMBODIMENT X |
| | 60 ± 5 mg | EMBODIMENT Y | EMBODIMENT Z | EMBODIMENT AA |
| | 70 ± 5 mg | EMBODIMENT AB | EMBODIMENT AC | EMBODIMENT AD |
| | 80 ± 5 mg | EMBODIMENT AE | EMBODIMENT AF | EMBODIMENT AG |
| | 90 ± 5 mg | EMBODIMENT AH | EMBODIMENT AI | EMBODIMENT AJ |
| | 100 ± 5 mg | EMBODIMENT AK | EMBODIMENT AL | EMBODIMENT AM |

In specific embodiments, the psilocybin mushroom includes at least one of *Copelandia*, *Gymnopilus*, *Inocybe*, *Panaeolus*, *Pholiotina*, *Pluteus*, and *Psilocybe*.

In specific embodiments, the *Cannabis* includes at least one of *Cannabis sativa*, *Cannabis indica*, and *Cannabis ruderalis*.

In specific embodiments, the plant biomass includes psilocybin mushroom.

In specific embodiments, the plant biomass includes psilocybin mushroom and *cannabis*.

In specific embodiments, the plant biomass includes psilocybin mushroom and *cannabis*, in a weight ratio of 1:99 to 25:75, respectively.

In specific embodiments, the plant biomass includes psilocybin mushroom and *cannabis*, in a weight ratio of 5:95 to 20:80, respectively.

In specific embodiments, the plant biomass includes psilocybin mushroom and *cannabis*, in a weight ratio of 10:90 to 25:75, respectively.

In specific embodiments, the plant biomass includes psilocybin mushroom and *cannabis*, in a weight ratio of 1:99 to 20:80, respectively.

In specific embodiments, the plant biomass includes psilocybin mushroom and *cannabis*, in a weight ratio of any one of embodiments I-XXV, as shown below.

| Embodiment | Weight ratio of psilocybin mushroom to cannabis, in plant biomass |
|---|---|
| I | <0.5:95.5 |
| II | 0.5:95.5 to 1:99 |
| III | 1:99 to 2:98 |
| IV | 2:98 to 3:97 |
| V | 3:97 to 4:96 |
| VI | 4:96 to 5:95 |
| VII | 5:95 to 10:90 |
| VIII | 10:90 to 15:85 |
| IX | 15:85 to 20:80 |
| X | 20:80 to 25:75 |
| XI | 25:75 to 30:70 |
| XII | 30:70 to 35:65 |
| XIII | 35:65 to 40:60 |
| XIV | 40:60 to 45:55 |
| XV | 45:55 to 50:50 |
| XVI | 50:50 to 55:45 |
| XVII | 55:45 to 60:40 |
| XVIII | 60:40 to 65:35 |
| XIX | 65:35 to 70:30 |
| XX | 70:30 to 75:25 |
| XXI | 75:25 to 80:20 |
| XXII | 80:20 to 85:15 |
| XXIII | 85:15 to 90:10 |
| XXIV | 90:10 to 95:5 |
| XXV | >95.5:0.5 |

In specific embodiments, the psilocybin mushroom has a moisture content of less than 15 wt. %.

In specific embodiments, the psilocybin mushroom has a moisture content of less than 10 wt. %.

In specific embodiments, the psilocybin mushroom has a moisture content of less than 5 wt. %.

In specific embodiments, the *cannabis* has a moisture content of less than 15 wt. %.

In specific embodiments, the *cannabis* has a moisture content of less than 10 wt. %.

In specific embodiments, the *cannabis* has a moisture content of less than 5 wt. %.

In specific embodiments, the reducing the size of the plant biomass is carried out such that at least 25 wt. % of the plant biomass is less than 50 mm.

In specific embodiments, the reducing the size of the plant biomass is carried out such that at least 50 wt. % of the plant biomass is less than 50 mm.

In specific embodiments, the reducing the size of the plant biomass is carried out such that at least 90 wt. % of the plant biomass is less than 50 mm.

In specific embodiments, the reducing the size of the plant biomass is carried out such that at least 25 wt. % of the psilocybin mushroom present in the plant biomass is less than 50 mm.

In specific embodiments, the reducing the size of the plant biomass is carried out such that at least 50 wt. % of the psilocybin mushroom present in the plant biomass is less than 50 mm.

In specific embodiments, the reducing the size of the plant biomass is carried out such that at least 90 wt. % of the psilocybin mushroom present in the plant biomass is less than 50 mm.

In specific embodiments, the reducing the size of the plant biomass is carried out such that at least 25 wt. % of the *cannabis* present in the plant biomass is less than 50 mm.

In specific embodiments, the reducing the size of the plant biomass is carried out such that at least 50 wt. % of the *cannabis* present in the plant biomass is less than 50 mm.

In specific embodiments, the reducing the size of the plant biomass is carried out such that at least 90 wt. % of the *cannabis* present in the plant biomass is less than 50 mm.

In specific embodiments, the reducing the size of the plant biomass is carried out such that at least 25 wt. % of the plant biomass is less than 10 mm.

In specific embodiments, the reducing the size of the plant biomass is carried out such that at least 50 wt. % of the plant biomass is less than 10 mm.

In specific embodiments, the reducing the size of the plant biomass is carried out such that at least 90 wt. % of the plant biomass is less than 10 mm.

In specific embodiments, the reducing the size of the plant biomass is carried out such that at least 25 wt. % of the psilocybin mushroom present in the plant biomass is less than 10 mm.

In specific embodiments, the reducing the size of the plant biomass is carried out such that at least 50 wt. % of the psilocybin mushroom present in the plant biomass is less than 10 mm.

In specific embodiments, the reducing the size of the plant biomass is carried out such that at least 90 wt. % of the psilocybin mushroom present in the plant biomass is less than 10 mm.

In specific embodiments, the reducing the size of the plant biomass is carried out such that at least 25 wt. % of the *cannabis* present in the plant biomass is less than 10 mm.

In specific embodiments, the reducing the size of the plant biomass is carried out such that at least 50 wt. % of the *cannabis* present in the plant biomass is less than 10 mm.

In specific embodiments, the reducing the size of the plant biomass is carried out such that at least 90 wt. % of the *cannabis* present in the plant biomass is less than 10 mm.

In specific embodiments, the reducing the size of the plant biomass is carried out employing at least one of blending, grinding, pulverizing, mincing, liquefying, cutting, macerating, and chopping.

In specific embodiments, the ultrasonicating employs high-power ultrasound waves.

In specific embodiments, the ultrasonicating employs high-power ultrasound waves effective to achieve ultrasound-assisted cell lysis.

In specific embodiments, the ultrasonicating employs high-power ultrasound waves effective to achieve ultrasound-assisted cell lysis of the psilocybin mushroom.

In specific embodiments, the contacting of the plant biomass with the supercritical fluid solvent system is a supercritical fluid extraction (SFE).

In specific embodiments, the supercritical fluid extraction (SFE) is carried out once.

In specific embodiments, the supercritical fluid extraction (SFE) is carried out multiple (e.g., 2 or more) times, such that it is a fractional supercritical fluid extraction (FSFE).

In specific embodiments, the supercritical fluid extraction (SFE) is a fractional supercritical fluid extraction (FSFE), wherein each SFE is independently carried out (i) at a different temperature, (ii) at a different pressure, (iii) with a different solvent system, or (iv) any combination thereof.

In specific embodiments, the contacting of the plant biomass with the supercritical fluid solvent system is carried out at a pressure of above 74 bar and wherein the supercritical fluid solvent system includes carbon dioxide ($CO_2$).

In specific embodiments, the contacting of the plant biomass with the supercritical fluid solvent system is carried out at a pressure of 75-500 bar and wherein the supercritical fluid solvent system includes carbon dioxide ($CO_2$).

In specific embodiments, the contacting of the plant biomass with the supercritical fluid solvent system is carried out at a pressure of 75-250 bar and wherein the supercritical fluid solvent system includes carbon dioxide ($CO_2$).

In specific embodiments, the contacting of the plant biomass with the supercritical fluid solvent system is carried out at a pressure of 75-150 bar and wherein the supercritical fluid solvent system includes carbon dioxide ($CO_2$).

In specific embodiments, the contacting of the plant biomass with the supercritical fluid solvent system is carried out at a temperature of above 31° C. and wherein the supercritical fluid solvent system includes carbon dioxide ($CO_2$).

In specific embodiments, the contacting of the plant biomass with the supercritical fluid solvent system is carried out at a temperature of 32-200° C. and wherein the supercritical fluid solvent system includes carbon dioxide ($CO_2$).

In specific embodiments, the contacting of the plant biomass with the supercritical fluid solvent system is carried out at a temperature of 32-150° C. and wherein the supercritical fluid solvent system includes carbon dioxide ($CO_2$).

In specific embodiments, the contacting of the plant biomass with the supercritical fluid solvent system is carried out at a temperature of 32-100° C. and wherein the supercritical fluid solvent system includes carbon dioxide ($CO_2$).

In specific embodiments, the contacting of the plant biomass with the supercritical fluid solvent system is carried out at a temperature of 32-75° C. and wherein the supercritical fluid solvent system includes carbon dioxide ($CO_2$).

In specific embodiments, the contacting of the plant biomass with the supercritical fluid solvent system is carried out for period of time of at least 30 seconds.

In specific embodiments, the contacting of the plant biomass with the supercritical fluid solvent system is carried out for period of time of at least 60 seconds.

In specific embodiments, the contacting of the plant biomass with the supercritical fluid solvent system is carried out for period of time of at least 5 minutes.

In specific embodiments, the contacting of the plant biomass with the supercritical fluid solvent system is carried out for period of time of 0.1-10 hours.

In specific embodiments, the contacting of the plant biomass with the supercritical fluid solvent system is carried out for period of time of 0.1-8 hours.

In specific embodiments, the contacting of the plant biomass with the supercritical fluid solvent system is carried out for period of time of 0.1-6 hours.

In specific embodiments, the contacting of the plant biomass with the supercritical fluid solvent system is carried out for period of time of 0.1-4 hours.

In specific embodiments, the contacting of the plant biomass with the supercritical fluid solvent system is carried out for period of time of 0.1-2 hours.

In specific embodiments, the contacting of the plant biomass with the supercritical fluid solvent system is carried out for period of time of 0.1-1 hour.

In specific embodiments, the contacting of the plant biomass with the supercritical fluid solvent system is carried out for period of time of 0.2-10 hours.

In specific embodiments, the contacting of the plant biomass with the supercritical fluid solvent system is carried out for period of time of 0.2-8 hours.

In specific embodiments, the contacting of the plant biomass with the supercritical fluid solvent system is carried out for period of time of 0.2-6 hours.

In specific embodiments, the contacting of the plant biomass with the supercritical fluid solvent system is carried out for period of time of 0.2-4 hours.

In specific embodiments, the contacting of the plant biomass with the supercritical fluid solvent system is carried out for period of time of 0.2-2 hours.

In specific embodiments, the contacting of the plant biomass with the supercritical fluid solvent system is carried out for period of time of 0.2-1 hour.

In specific embodiments, the supercritical fluid solvent system includes at least one of carbon dioxide ($CO_2$), hydrogen ($H_2$), neon (Ne), nitrogen ($N_2$), argon (Ar), methane ($CH_4$), ethane ($CH_3CH_3$), propane ($CH_3CH_2CH_3$), ammonia ($NH_3$), xenon (Xe), methanol, ethanol, 1-propanol, 2-propanol, 1-hexanol, 2-methoxy ethanol, tetrahydrofuran (THF), 1,4-dioxane, acetonitrile, acetic acid, methylene chloride, dichloroethane, chloroform, ethyl acetate, propylene carbonate, N,N-dimethylaceamide, dimethyl sulfoxide (DMSO), formic acid, carbon disulfide, acetone, toluene, hexanes, pentanes, trifluoromethane (Freon® 23), nitrous oxide ($N_2O$), sulfur hexafluroide ($SF_6$), butane (n-$C_4H_{10}$), isobutane (i-$C_4H_{10}$), ethyl ether (($C_2H_5)_{20}$), benzotrifluoride ($C_6H_5CF_3$), (p-chlorophenyl)trifluoromethane (Cl$C_6H_4CF_3$), chlorofluorocarbon (CFC), hydrofluorocarbon (HFA), and HFA-134a (1,1,1,2-tetrafluoroethane).

In specific embodiments, the supercritical fluid solvent system includes carbon dioxide ($CO_2$) and at least one of hydrogen ($H_2$), neon (Ne), nitrogen ($N_2$), argon (Ar), methane ($CH_4$), ethane ($CH_3CH_3$), propane ($CH_3CH_2CH_3$), ammonia ($NH_3$), xenon (Xe), methanol, ethanol, 1-propanol, 2-propanol, 1-hexanol, 2-methoxy ethanol, tetrahydrofuran (THF), 1,4-dioxane, acetonitrile, acetic acid, methylene chloride, dichloroethane, chloroform, ethyl acetate, propylene carbonate, N,N-dimethylaceamide, dimethyl sulfoxide (DMSO), formic acid, carbon disulfide, acetone, toluene, hexanes, pentanes, trifluoromethane (Freon® 23), nitrous oxide ($N_2O$), sulfur hexafluroide ($SF_6$), butane (n-$C_4H_{10}$), isobutane (i-$C_4H_{10}$), ethyl ether (($C_2H_5)_{20}$), benzotrifluoride ($C_6H_5CF_3$), (p-chlorophenyl)trifluoromethane (Cl$C_6H_4CF_3$), chlorofluorocarbon (CFC), hydrofluorocarbon (HFA), and HFA-134a (1,1,1,2-tetrafluoroethane).

In specific embodiments, the supercritical fluid solvent system includes carbon dioxide ($CO_2$) and at least one of acetic acid, ethanol, and methanol, In specific embodiments, the supercritical fluid solvent system includes carbon dioxide ($CO_2$) as the sole solvent.

In specific embodiments, the contacting of the plant biomass with the supercritical fluid solvent system is carried out in the absence of water.

In specific embodiments, the supercritical fluid solvent system does not include water.

In specific embodiments, the supercritical fluid solvent system includes less than 1 wt. % water.

In specific embodiments, the method of obtaining an extract further includes purifying the extract.

In specific embodiments, the method of obtaining an extract further includes purifying the extract employing at least one of chromatography, adsorption, crystallization, distillation, liquid-liquid extraction, filtration, fractional distillation, precipitation, recrystallization, lyophilization (freeze drying), and sublimation.

In specific embodiments, the method of obtaining an extract is carried out in a batch mode, within 8 hours.

In specific embodiments, the method of obtaining an extract is carried out in a batch mode, within 6 hours.

In specific embodiments, the method of obtaining an extract is carried out in a batch mode, within 5 hours.

In specific embodiments, the method of obtaining an extract is carried out in a batch mode, within 4 hours.

In specific embodiments, the method of obtaining an extract is carried out in a batch mode, within 2.5 hours.

In specific embodiments, the method of obtaining an extract is carried out in a batch mode, within 2 hours.

In specific embodiments, the method of obtaining an extract is carried out in a batch mode, within 1.5 hour.

In specific embodiments, the method of obtaining an extract is carried out in a batch mode, within 1 hour.

In specific embodiments, the extract of the plant biomass is administered neat, without any excipients.

In specific embodiments, the extract of the plant biomass is administered as a pharmaceutical product, as an oral dissolvable film (ODF), as a nutraceutical product, and/or as an edible product.

In specific embodiments, the extract of the plant biomass is administered as an oral dissolvable film (ODF).

In specific embodiments, the extract is formulated into at least one of a pharmaceutical product, an oral dissolvable film (ODF), a nutraceutical product, and an edible product.

In specific embodiments, the extract is formulated into an oral dissolvable film (ODF).

In specific embodiments, the pharmaceutical product includes (i) one or more pharmaceutically acceptable excipients and (ii) the extract.

In specific embodiments, the oral dissolvable film (ODF) includes (i) one or more pharmaceutically acceptable excipients and (ii) the extract.

In specific embodiments, the oral dissolvable film (ODF) includes (i) a film-forming matrix that includes one or more polymers and (ii) the extract.

In specific embodiments, the film-forming matrix includes a flowable water-soluble or water swellable film-forming polymer.

In specific embodiments, the flowable water-soluble or water swellable film-forming matrix that includes one or more polymers includes: plasticizer, binder, preservative, solvent, coloring agent, flavoring agent, sweetening agent, filler, bulking agent, saliva stimulating agent, stabilizing and thickening agent, gelling agent, taste masking agent, pigment, lubricant, release modifier, adjuvant, solubilizer & emulsifier, fragrance, emulsifier, surfactant, pH adjusting agent, buffering agent, lipid, glidant, stabilizer, antioxidant, anti-tacking agent, and humectant, permeation enhancer, bitter masking agent, mucoadhesive agent, disintegrant, oil, medium chain triglyceride, or any combination thereof.

In specific embodiments, the oral dissolvable film includes: (a) plasticizer, (b) solvent, (c) sweetener, (d) flavoring agent, (e) binder, (f) coloring agent, (g) preservative, and (h) the extract.

In specific embodiments, the oral dissolvable film includes: rapidly dissolving binder including polyvinyl alcohol (PVA) and polyvinyl alcohol (PVA)-polyethylene glycol (PEG) copolymer; film forming polymer including hydroxypropyl methyl cellulose (HPMC); a moisture deterring polymer including aminoalkyl methacrylate copolymers; and the extract.

In specific embodiments, the oral dissolvable film has a moisture content of less than 10 wt. %.

In specific embodiments, the oral dissolvable film has a moisture content of less than 8 wt. %.

In specific embodiments, the oral dissolvable film has a moisture content of less than 6 wt. %.

In specific embodiments, the oral dissolvable film has a moisture content of less than 5 wt. %.

In specific embodiments, the moisture deterring polymer includes EUDRAGIT® EPO (aminoalkyl methacrylate copolymers).

In specific embodiments, the moisture deterring polymer includes 1-4 wt. % EUDRAGIT® EPO (aminoalkyl methacrylate copolymers).

In specific embodiments, the rapidly dissolving binder includes Kollicoat® Protect (polyvinyl alcohol (PVA) and polyvinyl alcohol (PVA)-polyethylene glycol (PEG) copolymer).

In specific embodiments, the rapidly dissolving binder includes 25-80 wt. % Kollicoat® Protect (polyvinyl alcohol (PVA) and polyvinyl alcohol (PVA)-polyethylene glycol (PEG) copolymer).

In specific embodiments, the film forming polymer includes hypromellose (hydroxypropyl methyl cellulose (HPMC)).

In specific embodiments, the film forming polymer includes 5-20 wt. % hypromellose (hydroxypropyl methyl cellulose (HPMC)).

In specific embodiments, the oral dissolvable film further includes at least one of plasticizer, binder, preservative, solvent, coloring agent, flavoring agent, sweetening agent, filler, bulking agent, saliva stimulating agent, stabilizing and thickening agent, gelling agent, taste masking agent, pigment, lubricant, release modifier, adjuvant, solubilizer & emulsifier, fragrance, emulsifier, surfactant, pH adjusting agent, buffering agent, lipid, glidant, stabilizer, antioxidant, anti-tacking agent, and humectant, permeation enhancer, bitter masking agent, mucoadhesive agent, disintegrant, oil, and medium chain triglyceride.

In specific embodiments, upon contact with the oral cavity, the oral dissolvable film disintegrates within 120 seconds.

In specific embodiments, upon contact with the oral cavity, the oral dissolvable film disintegrates within 90 seconds.

In specific embodiments, upon contact with the oral cavity, the oral dissolvable film disintegrates within 60 seconds.

In specific embodiments, upon contact with the oral cavity, the oral dissolvable film disintegrates within 45 seconds.

In specific embodiments, upon contact with the oral cavity, the oral dissolvable film disintegrates within 30 seconds.

In specific embodiments, upon contact with the oral cavity, the oral dissolvable film disintegrates in 5-120 seconds.

In specific embodiments, upon contact with the oral cavity, the oral dissolvable film disintegrates in 5-90 seconds.

In specific embodiments, upon contact with the oral cavity, the oral dissolvable film disintegrates in 5-60 seconds.

In specific embodiments, upon contact with the oral cavity, the oral dissolvable film disintegrates in 5-45 seconds.

In specific embodiments, upon contact with the oral cavity, the oral dissolvable film disintegrates in 5-30 seconds.

In specific embodiments, the oral dissolvable film has a mass of less than 250 mg.

In specific embodiments, the oral dissolvable film has a mass of less than 225 mg.

In specific embodiments, the oral dissolvable film has a mass of less than 200 mg.

In specific embodiments, the oral dissolvable film has a mass of 100-250 mg.

In specific embodiments, the oral dissolvable film has a mass of 100-225 mg.

In specific embodiments, the oral dissolvable film has a mass of 100-200 mg.

In specific embodiments, the oral dissolvable film has a mass of 150-250 mg.

In specific embodiments, the oral dissolvable film has the following dimensions: 44±6 mm×22±3 mm×0.12±0.02 mm.

In specific embodiments, the oral dissolvable film has a thickness of less than 0.350 mm.

In specific embodiments, the oral dissolvable film exhibits a stability such that at least 80 wt. % of active ingredient(s) remain after 30 days at 45° C. and 65% relative humidity.

In specific embodiments, the oral dissolvable film exhibits a stability such that at least 90 wt. % of active ingredient(s) remain after 30 days at 45° C. and 65% relative humidity.

In specific embodiments, the oral dissolvable film exhibits a stability such that at least 95 wt. % of active ingredient(s) remain after 30 days at 45° C. and 65% relative humidity.

In specific embodiments, the nutraceutical product includes (i) one or more nutraceutically acceptable excipients and (ii) the extract.

In specific embodiments, the edible product includes (i) one or more edible (e.g., GRAS) excipients and (ii) the extract.

In specific embodiments, the psychological or neurological disorder comprises at least one of obsessive compulsive disorder (OCD), depression, pain, irritability, fibromyalgia, post-traumatic stress disorder (PTSD), cluster headaches, paranoia, anorexia, psychosis, anxiety, panic attacks, flashbacks, smoking addiction, alcohol addiction, cocaine addiction, and nausea or sickness associated with chemotherapy.

In specific embodiments, the oral dissolvable film includes a low dose or microdose of the psychedelic compound.

In specific embodiments, the oral dissolvable film includes a low dose or microdose of the psychedelic compound, wherein the low dose or microdose of the psychedelic compound is sub-threshold or sub-therapeutic.

In specific embodiments, the oral dissolvable film includes a low dose or microdose of the psychedelic compound, wherein the low dose or microdose of the psychedelic compound is sub-threshold or sub-therapeutic, insufficient to produce whole-body effects, but is high enough to allow the cellular response to be observed.

In specific embodiments, a unit dose of the oral dissolvable film includes THC and at least one of psilocin, psilocybin, and baeocystin, as provided in any one of EMBODIMENTS A-AM shown below.

|  |  | Amount of psilocin, psilocybin, and baeocystin (aggregate) | | |
|---|---|---|---|---|
|  |  | 10-30 mcg (microdose) | 10 ± 2 mg (low dose) | 25 ± 5 mg (high dose) |
| Amount of THC | 1 ± 0.5 mg | EMBODIMENT A | EMBODIMENT B | EMBODIMENT C |
|  | 2.5 ± 1.5 mg | EMBODIMENT D | EMBODIMENT E | EMBODIMENT F |
|  | 5 ± 2.5 mg | EMBODIMENT G | EMBODIMENT H | EMBODIMENT I |
|  | 10 ± 5 mg | EMBODIMENT J | EMBODIMENT K | EMBODIMENT L |
|  | 20 ± 5 mg | EMBODIMENT M | EMBODIMENT N | EMBODIMENT O |
|  | 30 ± 5 mg | EMBODIMENT P | EMBODIMENT Q | EMBODIMENT R |
|  | 40 ± 5 mg | EMBODIMENT S | EMBODIMENT T | EMBODIMENT U |
|  | 50 ± 5 mg | EMBODIMENT V | EMBODIMENT W | EMBODIMENT X |
|  | 60 ± 5 mg | EMBODIMENT Y | EMBODIMENT Z | EMBODIMENT AA |
|  | 70 ± 5 mg | EMBODIMENT AB | EMBODIMENT AC | EMBODIMENT AD |
|  | 80 ± 5 mg | EMBODIMENT AE | EMBODIMENT AF | EMBODIMENT AG |
|  | 90 ± 5 mg | EMBODIMENT AH | EMBODIMENT AI | EMBODIMENT AJ |
|  | 100 ± 5 mg | EMBODIMENT AK | EMBODIMENT AL | EMBODIMENT AM |

In specific embodiments, the extract of the plant biomass is administered to improve creativity, boost physical energy level, attain emotional balance, increase performance on problems-solving tasks, to treat anxiety, to treat depression, to treat addiction, to treat pain, to treat nausea, or any combination thereof.

In specific embodiments, the extract of the plant biomass is administered to treat at least one of obsessive compulsive disorder (OCD), depression, pain, irritability, fibromyalgia, post-traumatic stress disorder (PTSD), cluster headaches, paranoia, anorexia, psychosis, anxiety, panic attacks, flashbacks, smoking addiction, alcohol addiction, cocaine addiction, and nausea or sickness associated with chemotherapy.

In specific embodiments, the extract of the plant biomass is administered to treat at least one of treatment resistant depression, major depression disorder, generalized anxiety, and end of life-palliative care.

In specific embodiments, the psychedelic compound includes at least one of psilocin, psilocybin, and baeocystin.

In specific embodiments, the cannabinoid includes THC.

In specific embodiments, 1-5 oral dissolvable films are administered a day.

In specific embodiments, the one or more active pharmaceutical ingredients (APIs) are delivered via enterally, orally (PO), buccally, transmucosally, or sublingually.

In specific embodiments, the oral dissolvable film is administered orally.

In specific embodiments, a microdose of 10-30 mcg in the aggregate of psilocin, psilocybin, and baeocystin is administered orally.

In specific embodiments, a microdose of 20±10 mcg in the aggregate of psilocin, psilocybin, and baeocystin is administered orally.

In specific embodiments, a low dose of 10 mg in the aggregate of psilocin, psilocybin, and baeocystin is administered orally.

In specific embodiments, a low dose of 10±2 mg in the aggregate of psilocin, psilocybin, and baeocystin is administered orally.

In specific embodiments, a high dose of 25 mg in the aggregate of psilocin, psilocybin, and baeocystin is administered orally.

In specific embodiments, a high dose of 25±5 mg in the aggregate of psilocin, psilocybin, and baeocystin is administered orally.

In specific embodiments, the dosing regimen includes (i) a low dose of psilocin, psilocybin, and/or baeocystin administered orally, (ii) followed by a high dose of psilocin, psilocybin, and/or baeocystin administered orally, (iii) followed by a microdose of psilocin, psilocybin, and/or baeocystin administered orally.

In specific embodiments, the dosing regimen includes (i) a low dose of psilocin, psilocybin, and/or baeocystin administered orally, (ii) followed 7±2 days later by a high dose of psilocin, psilocybin, and/or baeocystin administered orally, (iii) followed by a microdose of psilocin, psilocybin, and/or baeocystin once every 4±1 days, administered orally.

In specific embodiments, the dosing regimen includes (i) a low dose of psilocin, psilocybin, and/or baeocystin administered orally, (ii) followed by a high dose of psilocin, psilocybin, and/or baeocystin administered orally, (iii) followed by a microdose of psilocin, psilocybin, and/or baeocystin once every 4±1 days, administered orally.

In specific embodiments, the oral dissolvable film includes THC and a microdose of 10-30 mcg in the aggregate of psilocin, psilocybin, and baeocystin.

In specific embodiments, the oral dissolvable film includes THC and a microdose of 20±10 mcg in the aggregate of psilocin, psilocybin, and baeocystin.

In specific embodiments, the oral dissolvable film includes THC and a low dose of 10 mg in the aggregate of psilocin, psilocybin, and baeocystin.

In specific embodiments, the oral dissolvable film includes THC and a low dose of 10±2 mg in the aggregate of psilocin, psilocybin, and baeocystin.

In specific embodiments, the oral dissolvable film includes THC and a high dose of 25 mg in the aggregate of psilocin, psilocybin, and baeocystin.

In specific embodiments, the oral dissolvable film includes THC and a high dose of 25±5 mg in the aggregate of psilocin, psilocybin, and baeocystin.

In specific embodiments, the oral dissolvable film includes 1-100 mg THC and a microdose of 10-30 mcg in the aggregate of psilocin, psilocybin, and baeocystin.

In specific embodiments, the oral dissolvable film includes 1-100 mg THC and a microdose of 20±10 mcg in the aggregate of psilocin, psilocybin, and baeocystin.

In specific embodiments, the oral dissolvable film includes 1-100 mg THC and a low dose of 10 mg in the aggregate of psilocin, psilocybin, and baeocystin.

In specific embodiments, the oral dissolvable film includes 1-100 mg THC and a low dose of 10±2 mg in the aggregate of psilocin, psilocybin, and baeocystin.

In specific embodiments, the oral dissolvable film includes 1-100 mg THC and a high dose of 25 mg in the aggregate of psilocin, psilocybin, and baeocystin.

In specific embodiments, the oral dissolvable film includes 1-100 mg THC and a high dose of 25±5 mg in the aggregate of psilocin, psilocybin, and baeocystin.

The invention claimed is:

1. A method for obtaining an extract, the method comprising:
   (a) reducing the size of a plant biomass, the plant biomass comprising psilocybin mushroom and *cannabis*;
   (b) ultrasonicating the plant biomass;
   (c) contacting the plant biomass with a supercritical fluid solvent system above the critical pressure and above the critical temperature; and
   (d) removing the supercritical fluid solvent system from the plant biomass to obtain an extract of psilocybin mushroom and *cannabis*;
   wherein,
   the plant biomass comprises the psilocybin mushroom and the *cannabis* in a weight ratio of 1:99 to 25:75, respectively.

2. The method of claim 1, wherein the psilocybin mushroom comprises at least one of *Copelandia, Gymnopilus, Inocybe, Panaeolus, Pholiotina, Pluteus,* and *Psilocybe.*

3. The method of claim 1, wherein the *cannabis* comprises at least one of *Cannabis sativa, Cannabis indica,* and *Cannabis ruderalis.*

4. The method of claim 1, wherein the psilocybin mushroom has a moisture content of less than 15 wt. %.

5. The method of claim 1, wherein the *cannabis* has a moisture content of less than 15 wt. %.

6. The method of claim 1, wherein the psilocybin mushroom is reduced to a size such that at least 90 wt. % of the psilocybin mushroom present in the plant biomass is less than 10 mm.

7. The method of claim 1, wherein the *cannabis* is reduced to a size such that at least 90 wt. % of the *cannabis* present in the plant biomass is less than 50 mm.

8. The method of claim 1, wherein the reducing the size of the plant biomass comprises at least one of blending, grinding, pulverizing, mincing, liquefying, cutting, macerating, and chopping.

9. The method of claim 1, wherein the ultrasonicating employs high-power ultrasound waves effective to achieve ultrasound-assisted cell lysis.

10. The method of claim 1, wherein the contacting of the plant biomass with the supercritical fluid solvent system is a supercritical fluid extraction (SFE), carried out once.

11. The method of claim 1, wherein the contacting of the plant biomass with the supercritical fluid solvent system is a fractional supercritical fluid extraction (FSFE), carried out multiple times.

12. The method of claim 1, wherein the contacting of the plant biomass with the supercritical fluid solvent system is carried out at a pressure of above 74 bar and wherein the supercritical fluid solvent system comprises carbon dioxide ($CO_2$).

13. The method of claim 1, wherein the contacting of the plant biomass with the supercritical fluid solvent system is carried out at a temperature of above 31° C. and wherein the supercritical fluid solvent system comprises carbon dioxide ($CO_2$).

14. The method of claim 1, wherein the contacting the plant biomass with the supercritical fluid solvent system is carried out for period of time of at least 60 seconds.

15. The method of claim 1, wherein the supercritical fluid solvent system comprises carbon dioxide ($CO_2$) and at least one of hydrogen ($H_2$), neon (Ne), nitrogen ($N_2$), argon (Ar), methane ($CH_4$), ethane ($CH_3CH_3$), propane ($CH_3CH_2CH_3$), ammonia ($NH_3$), xenon (Xe), methanol, ethanol, 1-propanol, 2-propanol, 1-hexanol, 2-methoxy ethanol, tetrahydrofuran (THF), 1,4-dioxane, acetonitrile, acetic acid, methylene chloride, dichloroethane, chloroform, ethyl acetate, propylene carbonate, N,N-dimethylaceamide, dimethyl sulfoxide (DMSO), formic acid, carbon disulfide, acetone, toluene, hexanes, pentanes, trifluoromethane (Freon® 23), nitrous oxide ($N_2O$), sulfur hexafluoride ($SF_6$), butane (n-$C_4H_{10}$), isobutane (i-$C_4H_{10}$), ethyl ether (($C_2H_5)_{20}$), benzotrifluoride ($C_6H_5CF_3$), (p-chlorophenyl)trifluoromethane (Cl$C_6H_4CF_3$), chlorofluorocarbon (CFC), hydrofluorocarbon (HFA), and HFA-134a (1,1,1,2-tetrafluoroethane).

16. The method of claim 1, wherein the supercritical fluid solvent system comprises carbon dioxide ($CO_2$) as the sole solvent.

17. The method of claim 1, further comprising purifying the extract.

18. The method of claim 1, further comprising purifying the extract employing at least one of chromatography, adsorption, crystallization, distillation, liquid-liquid extraction, filtration, fractional distillation, precipitation, recrystallization, lyophilization (freeze drying), and sublimation.

19. The method of claim 1, wherein relative to the plant biomass, the extract is enriched with cannabinoids.

20. The method of claim 1, wherein relative to the plant biomass, the extract is enriched with at least one of psilocybin, psilocin, and baeocystin.

21. The method of claim 1, wherein relative to the plant biomass, the extract is enriched with terpenes.

22. The method of claim 1, wherein relative to the plant biomass, the extract is enriched with flavonoids.

23. A method for obtaining an extract, the method comprising:
   (a) reducing the size of a plant biomass, the plant biomass comprising psilocybin mushroom and *cannabis*;
   (b) ultrasonicating the plant biomass;
   (c) contacting for period of time of at least 60 seconds the plant biomass with a supercritical fluid solvent system that comprises carbon dioxide ($CO_2$), at a pressure of above 74 bar, and at a temperature of above 31° C.; and
   (d) removing the supercritical fluid solvent system from the plant biomass to obtain an extract of psilocybin mushroom and *cannabis*;
   wherein,
   relative to the plant biomass, the extract is enriched with cannabinoids;
   relative to the plant biomass, the extract is enriched with at least one of psilocybin, psilocin, and baeocystin;
   relative to the plant biomass, the extract is enriched with terpenes; and
   relative to the plant biomass, the extract is enriched with flavonoids.

24. The method of claim 23, wherein
   relative to the *cannabis*, the extract is enriched with cannabinoids;
   relative to the *cannabis*, the extract is enriched with terpenes;
   relative to the *cannabis*, the extract is enriched with flavonoids; and relative to the psilocybin mushroom, the extract is enriched with at least one of psilocybin, psilocin, and baeocystin.

25. The method of claim 23, wherein on a weight percentage basis relative to the *cannabis*, the extract comprises at least 25 wt. % more cannabinoids;

relative to the *cannabis*, the extract comprises at least 25 wt. % more terpenes;

relative to the *cannabis*, the extract comprises at least 25 wt. % more flavonoids; and relative to the psilocybin mushroom, the extract comprises in the aggregate at least 25 wt. % more psilocybin, psilocin, and baeocystin.

\* \* \* \* \*